United States Patent [19]

Smith

[11] Patent Number: 5,098,256

[45] Date of Patent: Mar. 24, 1992

[54] VISCOUS SEAL BLOOD PUMP

[75] Inventor: William A. Smith, Lyndhurst, Ohio

[73] Assignee: The Cleveland Clinic Foundation, Cleveland, Ohio

[21] Appl. No.: 439,853

[22] Filed: Nov. 21, 1989

[51] Int. Cl.⁵ .............................................. F01D 11/04
[52] U.S. Cl. ..................................... 415/111; 415/900; 277/3; 600/16
[58] Field of Search ................ 415/110, 111, 900, 112; 277/3; 600/16, 17; 623/3

[56] References Cited

U.S. PATENT DOCUMENTS

| | | | |
|---|---|---|---|
| 2,448,717 | 9/1948 | Jeffcock | 415/110 |
| 4,135,253 | 1/1979 | Reich et al. | 415/112 |
| 4,196,910 | 4/1980 | Aizu | 415/111 |
| 4,243,230 | 1/1981 | Baker et al. | 277/3 |
| 4,384,725 | 5/1983 | Nenov | 277/3 |
| 4,589,822 | 5/1986 | Clausen et al. | 415/112 |
| 4,625,712 | 12/1986 | Wampler | 415/900 |
| 4,704,121 | 11/1987 | Moise | 415/112 |
| 4,927,407 | 5/1990 | Dorman | 623/3 |

Primary Examiner—John T. Kwon
Attorney, Agent, or Firm—Fay, Sharpe, Beall, Fagan, Minnich & McKee

[57] ABSTRACT

A blood pump includes a housing having an inlet and outlet communicating with a pump chamber. A rotor received in the pump chamber is rotated by a drive motor. A drive shaft extending between the motor and rotor is sealed by a fluid seal. The housing includes an opening defining a clearance with the drive shaft on the order of one or two thousandth (0.002) of an inch. A viscous, biocompatible fluid is utilized as the seal fluid.

17 Claims, 4 Drawing Sheets

VISCOUS SEAL BLOOD PUMP

BACKGROUND OF THE INVENTION

This invention pertains to the art of blood pumps and more particularly to rotary blood pumps. The invention is applicable to a seal arrangement for rotary blood pumps and will be described with particular reference thereto. However, it will be appreciated that the invention has broader applications and may be advantageously employed in other rotary mechanisms particularly adapted for biocompatible and medicinal purposes.

Rotary blood pumps are well known in the art as exhibited by the following U.S. Pat. Nos.:
Reich, et al. - U.S. Pat. No. 4,135,253
Wampler - U.S. Pat. No. 4,625,712
Moise - U.S. Pat. No. 4,704,121.
Each of the structures described in the patents has various advantages and drawbacks over other rotary blood pumps. Nevertheless, all are deemed to be particularly adapted to cardiac assist.

A primary concern in the rotary blood pump technology is the need for an effective seal between a rotary member and its associated stationary housing. In Reich, et al. a polymer lip on a baffle plate cooperates with an impeller shaft to limit blood flow from a pump chamber into a rotor chamber. A saline solution is preferably circulated throughout the rotor chamber for lubrication purposes and thus comes in contact with the seal along the impeller drive shaft. The saline solution is maintained under pressure and can prevent blood in the pump chamber from entering the rotor chamber. The pressurized saline produces a reverse flow of saline solution from the rotor chamber to the pump chamber. Per Reich, et al., a purge flow on the order of 20 ml/day can be expected. This saline flow produces a small separation between the stationary and moving seal components, as a result of the pressure and elasticity of the polymer lip on the baffle plate. Since saline solution is biocompatible, such a reverse flow has no adverse effect on the patient.

The Moise and Wampler patents are commonly assigned and illustrate two types of rotary blood pumps; namely, a radial flow pump in Moise and an axial flow pump in Wampler. Both of these patents also disclose the use of a purge seal utilizing a biocompatible fluid between rotary and stationary members similar in function to the seal and saline arrangement in Reich, et al.

In Wampler, the areas of potential contact are between the face seal and the stator hub, and the bearing flange and the hub. A balance between the external forces, the pressure forces, and hydrodynamic action between the contacting faces finally determines the relative clearances. In Moise, the stationary and moving seal surfaces are to be so manufactured and supported that there is a fixed, uniform clearance of micron-sized order of magnitude between these components. In all three patents discussed above, a fluid such as saline or a blood filtrate is intended to flow through the seal gap providing cooling, a flushing action to prevent cell build-up, and lubrication of the near-contact.

Although in theory and limited application such a purge seal arrangement may be effective, it also has drawbacks. A primary disadvantage to the prior art arrangements is the use of a contact-type seal for sealing along the drive shaft. Contact-type seals have the obvious disadvantage of wearing over time. Such wearing is highly critical when the fluid being handled is blood and the consequences of contamination, hemolysis, thrombosis, and the like could result. Heat is also generated at the contact points. Additionally, the disclosed contact-type seals (Reich, et al. and Wampler) can have a variable gap and leakage flow due to the many factors involved in their equilibration at working conditions.

The Moise seal arrangements already known in the art are unworkable from a practical manufacturing standpoint. The requirement for close and uniform clearances between the housing and rotary members so as to limit purge flow into the blood stream becomes unreasonable. It simply is too expensive a procedure to maintain the close tolerances and still provide a cost effective rotary blood pump that effectively seals.

SUMMARY OF THE INVENTION

The present invention contemplates a new and improved fluid seal or purge seal arrangement in a blood pump.

According to the present invention, a blood pump includes a housing having an internal pump chamber communicating with an inlet and outlet. A rotor is received in the pump chamber and selectively rotated by a drive shaft connected to a motor. A fluid seal means is defined along the drive shaft to limit flow from the pump chamber. The housing includes an opening receiving the drive shaft and defining a fluid seal means clearance on the order of thousandths of an inch with the drive shaft, rather than millionths of a meter.

According to another aspect of the invention, the fluid seal means includes a viscous fluid that is biocompatible.

According to a further aspect of the invention, a labyrinth arrangement in the fluid seal means facilitates control of the viscous fluid.

A principal advantage of the invention resides in the ability to provide an adequate seal along the drive shaft of a rotary blood pump without contact in the blood region.

Another advantage of the invention is found in the enlarged clearances that facilitate manufacture of the blood pump without any significant adverse effect on the sealing capabilities.

Still another advantage is realized by the cooling effect of the viscous fluid used in the fluid seal means.

Yet another advantage is the biocompatibility of the sealing fluid and the capacity of the human body to utilize the sealing fluid without adverse effect.

Still other advantages and benefits of the invention will become more apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein.

DETAILED DESCRIPTION OF THE PREFERRED EMBODIMENTS

Figure 1:
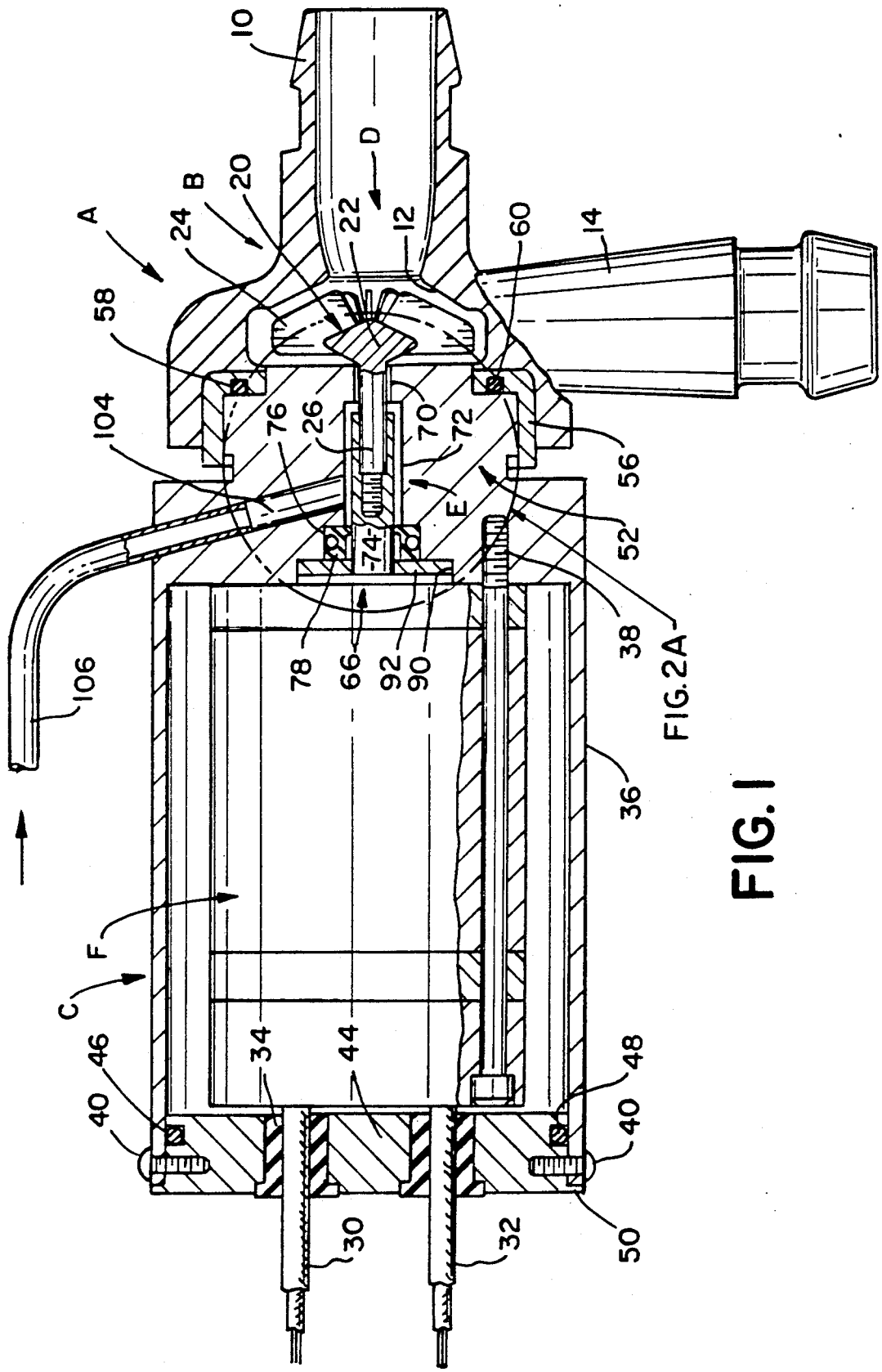
FIG. 1 is a longitudinal cross-sectional view of a blood pump according to the subject invention.

Referring now to the drawings wherein the showings are for purposes of illustrating the preferred embodiments of the invention only and not for purposes of limiting same, the FIGS. show a blood pump A including a pump housing B and a motor housing C. The pump housing encloses a rotary pump D that is driven by a drive shaft E. The drive shaft E is, in turn, driven by a motor F.

More particularly, and as shown in FIG. 1, the blood pump housing B includes an axial inlet 10 communicating with an enlarged diameter pump chamber 12. Tangential outlet 14 receives blood from the periphery of the pump chamber after it has exited the rotary pump D. In the embodiments illustrated the rotary pump is a radial flow pump, although other rotary pumps are contemplated without departing from the scope and intent of the subject invention. Likewise, while the motor shown is an electric type, other types of prime movers are also contemplated within the scope of the current invention.

In the preferred radial flow pump, impeller 20 includes a central hub 22 and plural vanes or blades 24 extending generally radially outward from the hub. An impeller drive shaft 26 forms a portion of the drive shaft E and extends axially rearward from the hub into the motor housing as will be described further below. Blood enters the chamber through the inlet 10 and is directed toward the hub. Rotation of the impeller at rotational speeds on the order of 2000 to 12,000 rpm adds energy to the blood so that blood exits via the outlet 14 at a higher pressure. Since the pumping operation of roto-dynamic blood pumps is generally known and forms no aspect of the subject invention, further discussion herein is deemed unnecessary.

The motor F received in the motor housing is shown as a well-known electrical motor having electrical leads 30, 32. The leads pass through wall 34 at a first end of the housing to supply power to the motor. The motor is mounted within cavity 36 through use of securing means such as fasteners 38. Alternatively, the motor stator and rotor bearings can be directly mounted in the housing. This arrangement maintains the motor fixed relative to the housing and, more importantly, relative to the pump chamber. The wall 34 is selectively removable from the remainder of the motor housing through use of fasteners 40. Preferably, reduced diameter portion 44 of the wall is closely received in the cavity 36. The reduced diameter portion includes a peripheral groove 46 adapted to receive a seal member such as O-ring 48 therein. An enlarged diameter rim 50 integrally formed on the wall engages the terminal end of the motor housing to precisely locate the wall for receipt of fasteners 40.

The pump housing B is secured to an opposite or second end 52 of the motor housing. Preferably, a retaining collar 56 is bonded to the pump housing to provide a secure, sealed engagement and the bonded arrangement mounted on the motor housing. The retaining collar includes a groove 58 adapted to receive seal member 60 therein to provide a sealed arrangement.

The motor housing cavity 36 and the pump chamber 12 communicate through an axially extending opening 66 defined by a series of variable diameter portions. The variable diameter portions generally increase in dimension as the opening extends axially from the pump chamber toward the motor housing cavity. No uniformity of axial clearance is required. It is preferable, though, that succeeding portions be significantly larger than the first so that the major pressure drop is in the first portion.

Figure 2A:
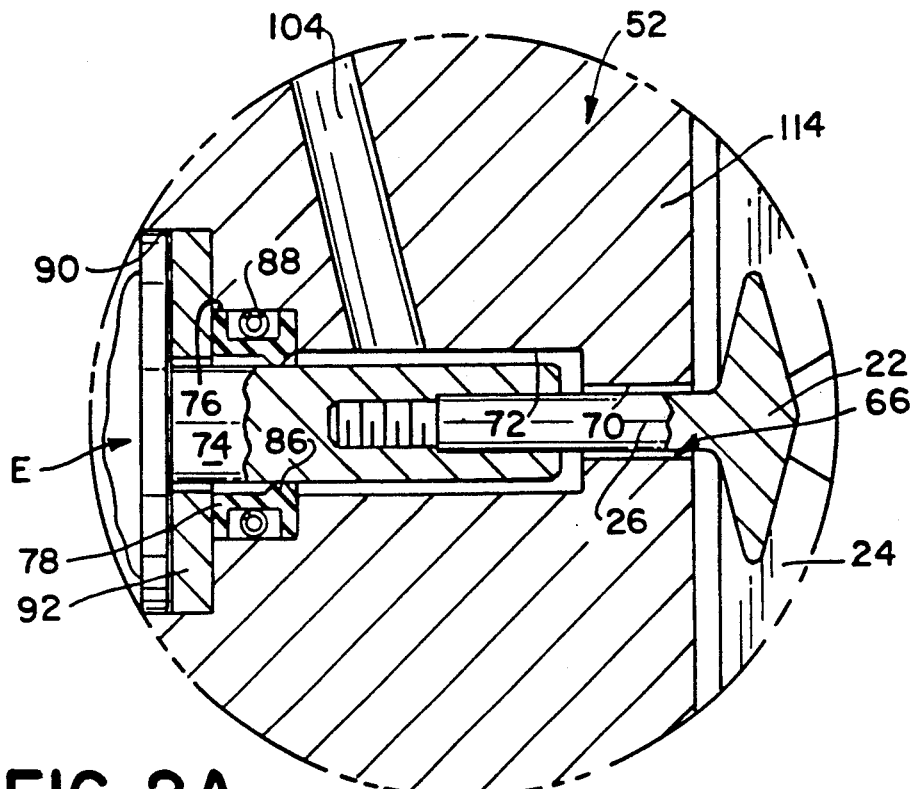
FIG. 2A is an enlarged cross-sectional view of the encircled area of FIG. 1.

More particularly, and with additional reference to FIG. 2A, a first portion 70 of the opening 66 extends axially rearwardly from the pump chamber. The small diameter of the first portion is adapted to closely receive the drive shaft 26 of the impeller therethrough. An opening second portion 72 is of increased diameter than the first portion. The second portion continues rearwardly toward the motor housing cavity, or leftwardly as illustrated. The enlarged diameter of the opening second portion accommodates a motor drive shaft 74, forming a second portion of the drive shaft E, extending from the motor. As will be understood, the drive shafts 26, 74 are secured in any conventional manner as will be appreciated by one skilled in the art. In the preferred arrangement, the motor drive shaft 74 threadedly receives the impeller drive shaft therein.

A third portion 76 of the opening is of slightly larger diametrical dimension than the second portion and adapted to receive a contact-type seal assembly 78 therein. Commercially available contact-type seal assembly 78 employs a lip seal 86 and O-ring 88 to limit flow from opening second portion 72 to the cavity 36. Since specific details of contact-type seal assemblies are already well known and do not form a part of the subject invention, further discussion is deemed unnecessary to a full and complete understanding of the invention.

Lastly, a fourth portion 90 of the opening receives a retaining ring 92. The retaining ring axially retains the contact-type seal assembly in the opening third portion. Alternatively, the lip seal 86 may be deleted and the motor cavity permitted to fill with seal fluid. Accordingly, if the lip seal assembly is eliminated, the opening second portion may be extended rearwardly to intersect the motor housing cavity and the third and fourth portions of the opening also become unnecessary.

In accordance with the first preferred embodiment shown in FIGS. 1 and 2A, the drive shaft 26 of the impeller and first portion 70 of the opening are sized to define a nominal radial clearance or gap on the order of one-thousandth (0.001) to two-thousandth (0.002) of an inch. The actual clearance may vary from near zero at one point of the circumference, to twice the nominal radial clearance at the diametrically opposite point on the circumference. It has been determined that this provides sufficient play between the drive shaft and the motor housing to accommodate tolerance buildup that occurs from manufacturing separate pump components. The second portion 72 of the opening is sized somewhat larger than the motor drive shaft 74 extending from the motor.

A fluid passage 104 extends generally radially through the motor housing to communicate with an external fluid source (not shown) through passage 106. The fluid source provides a supply of a biocompatible fluid that is used for sealing purposes along the drive shaft. A viscous biocompatible fluid is utilized due to the large dimensional clearance between the drive shaft and housing. The high viscosity (5 centipoise and greater) of the biocompatible fluid becomes an inherent part of the seal design which, in conjunction with the clearance between the housing and the rotating drive shaft, provides acceptable flow rates in addition to ease of manufacture.

Glycerol is one type of viscous biocompatible fluid that may be utilized for sealing along the drive shaft with the large clearance noted. Other biocompatible fluids include a glycerine or sugar solution with water or alcohol based solvents, or a blood substitute emulsion. At an approximate pump speed between 4000 and 6000 rpm, and a pressure on the viscous fluid of 20 to 70 millimeters of mercury, the leakage rate has been approximated at 0.1 cc/hour. This leakage rate is in the practical range without any adverse effect on a patient. Of course still other viscous, biocompatible fluids can be utilized without departing from the scope and intent of the subject invention. Leakage rates will vary with detail design and manufacture of the seal and viscous fluid chosen.

Figure 2B:
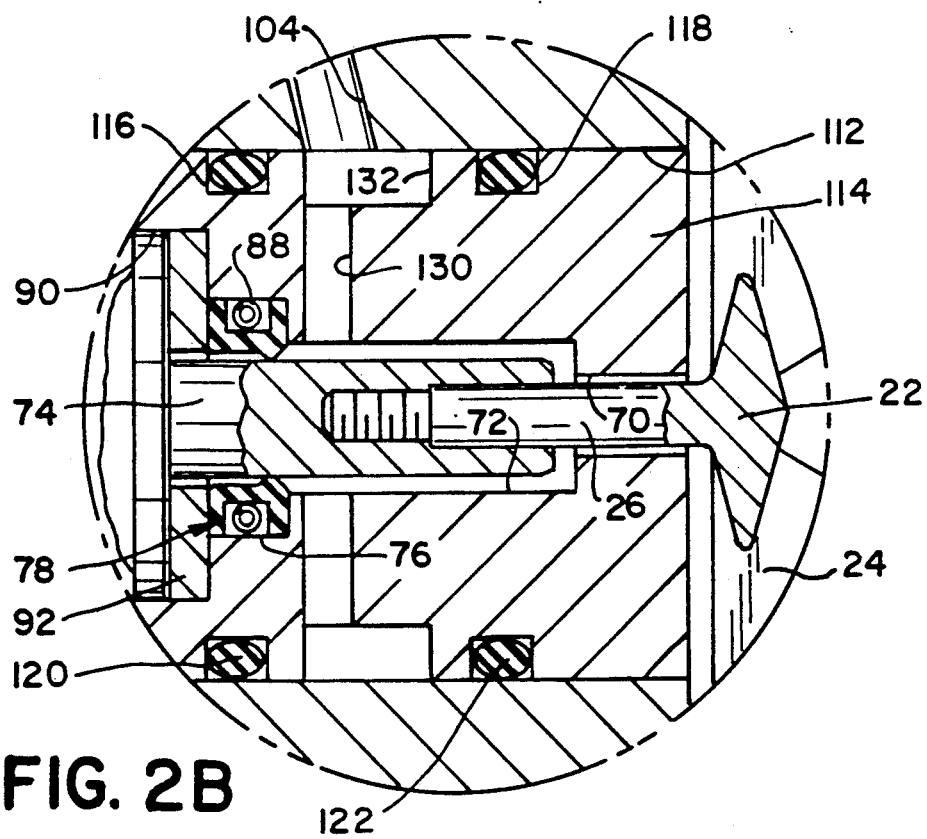
FIG. 2B is an enlarged cross-sectional view of the encircled area of FIG. 1 illustrating a first alternative fluid seal arrangement.

Referring now to FIG. 2B, a modified embodiment of the blood pump will be described in detail. For ease of illustration and understanding, like numerals will refer to like elements and new numerals are used to identify new elements. A single, enlarged opening 112 extends through the motor housing between the pump chamber and cavity. The opening 112 closely receives an insert 114. The insert includes first and second circumferentially continuous grooves 116, 118 defined on the periphery. The grooves are axially spaced and receive respective seal members such as O-rings 120, 122 for sealing between the insert 114 and the motor housing. Additionally, passage 104 in the housing is extended by forming a radial passage 130 in the insert. The passage includes an enlarged recess 132 along the outer peripheral portion of the insert. The recess provides a reservoir arrangement that facilitates fluid flow between passage 104 to the through opening 66 now formed in the insert.

A primary advantage of the insert arrangement is that the housing and insert may be manufactured from different materials. For example, a teflon insert may be used. The insert is simply press-fit into the housing opening. Since the insert includes a through opening having multi-diameter opening portions 70, 72, 76, 90 equivalent to the multi-diameter opening portions of the housing described in the FIG. 1 embodiment, receipt and operation of the drive shaft and seal assembly are substantially the same. Again, unless specifically noted otherwise, the remaining structure and operation of the blood pump are also substantially the same as that described with respect to the FIG. 1 embodiment.

Figure 3:
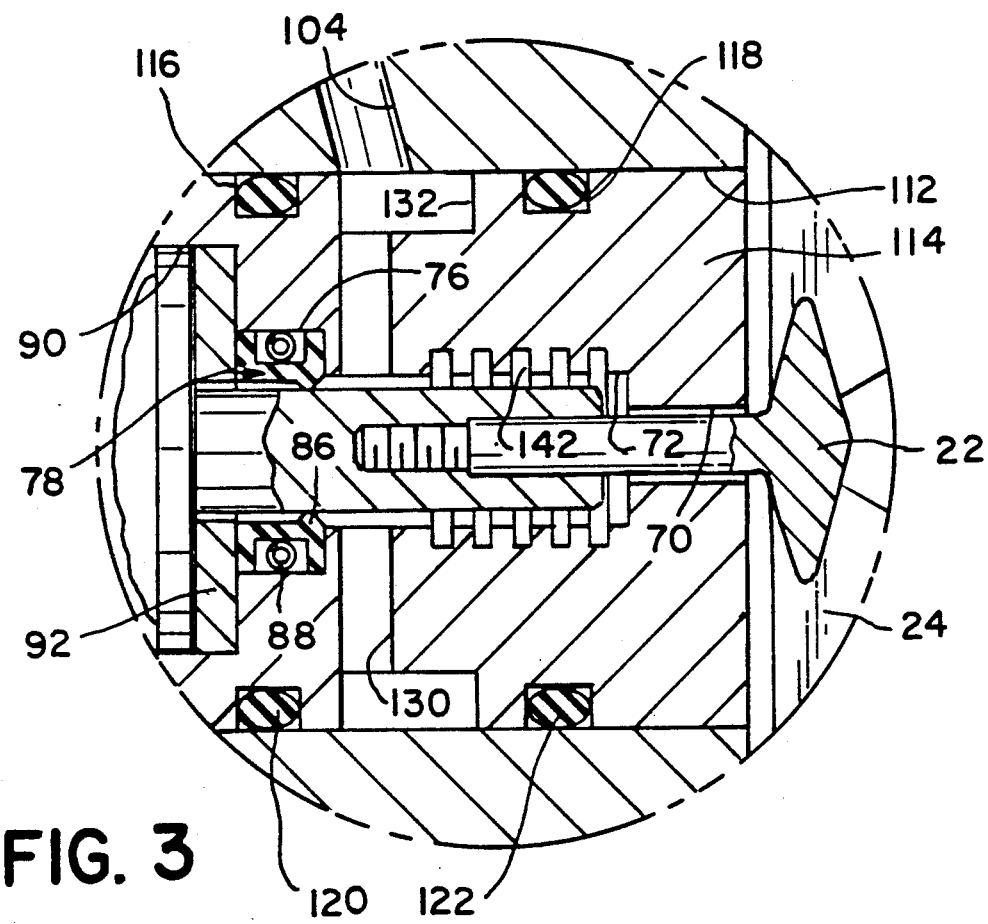
FIG. 3 is an enlarged cross-sectional view of the encircled area of FIG. 1 illustrating a second alternative fluid seal arrangement.

Turning now to FIG. 3, like numerals will again be used to refer to like elements, while new numerals will be used to refer to new elements. The insert 114 is substantially identical to the insert of FIG. 2B. It includes a multi-diameter opening having a first portion 70, second portion 72, third portion 76, and fourth portion 90 for providing an effective bearing and seal arrangement along the drive shaft. The through opening second portion, though, is modified to incorporate a labyrinth arrangement 142. Thus, a viscous fluid enters the motor housing through passage 104 which communicates with the enlarged recess 132 in the insert. The substantially radial passage 130 provides fluid communication between the recess and the second portion 70 of the through opening. The labyrinth arrangement 142 enhances the sealing properties of the viscous fluid prior to use of the fluid as a purge seal along the clearance defined between opening first portion 70 and the drive shaft.

Figure 4:
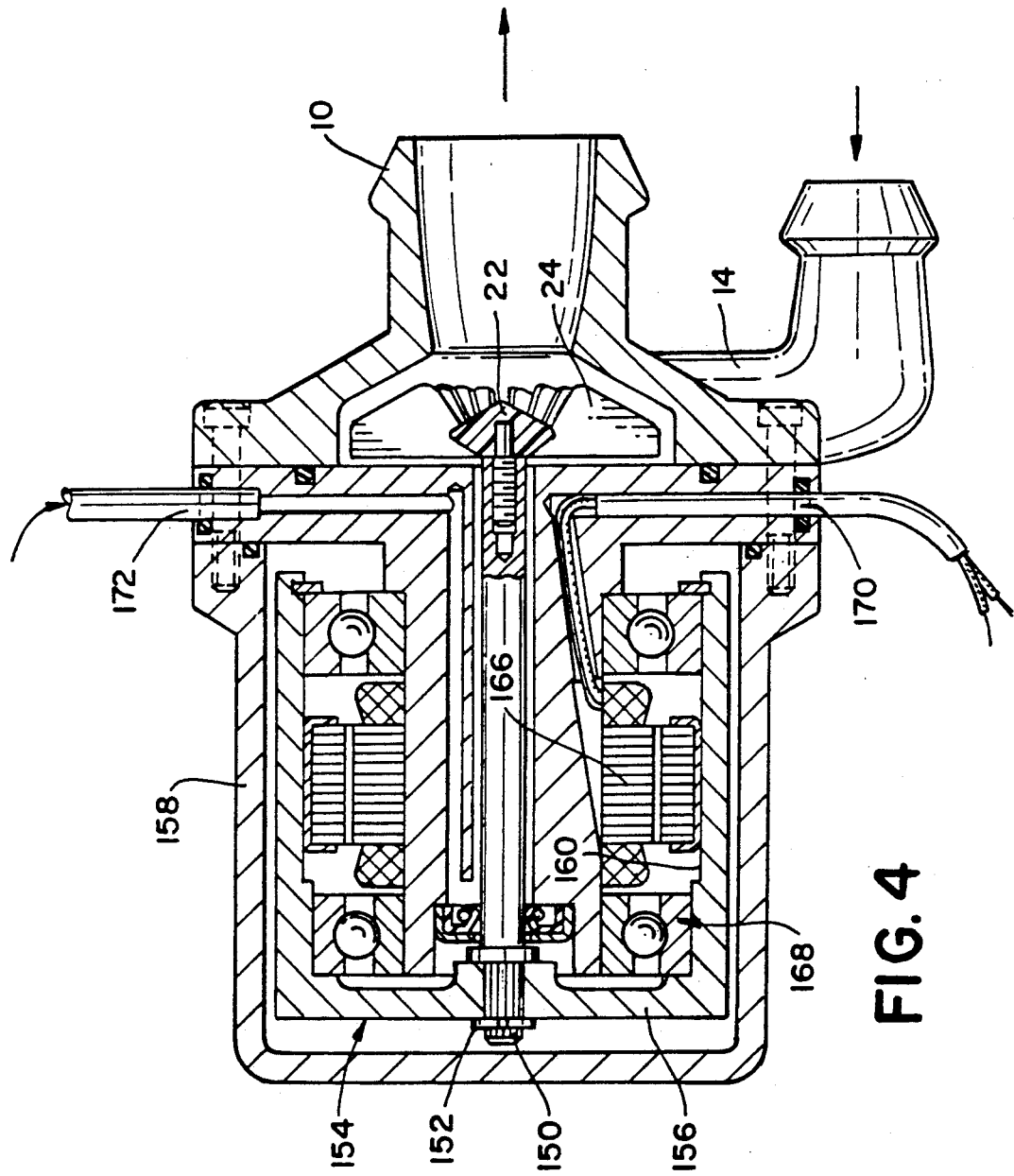
FIG. 4 is a longitudinal cross-sectional view of an alternate arrangement of a blood pump according to the subject invention.

In an effort to reduce the overall axial dimension of the rotary pump, the pump can be modified, for example, as shown in FIG. 4. The motor is adapted to contain or completely encompass the fluid seal path along the drive shaft. A remote end 150 of the drive shaft is splined and secured by fastening means such as retaining ring 152 to a rotor 154 of an inverted motor. The rotor includes a radial arm or series of arms 156 having a central opening adapted to receive the remote end of the drive shaft. The rotor arm also includes a longitudinal portion 158 that extends axially toward the pump chamber. The longitudinal portion has an enlarged recess 160 that closely receives the stator 166 of the motor. Interposed between the rotor and stator portions of the motor is a conventional bearing assembly 168 that permits free rotation of the rotor relative to the stator.

Two passages 170, 172 are defined through the sidewall of the housing. The first passage 170 receives electrical leads therethrough for selectively energizing the stator. The second passage 172 defines a fluid supply line that inlets the viscous seal fluid radially inward between the impeller shaft and the motor stator. The sealing fluid travels radially inward then travels axially from one end of the motor to the other before introduction to the exterior surface of the impeller shaft.

Incorporating the impeller shaft within the motor as in FIG. 4 significantly reduces the overall axial dimension of the blood pump without substantially increasing the diameter thereof. In other respects, the pump, and particularly the viscous fluid seal arrangement, operates in substantially the same manner as the pump embodiments described above.

The invention has been described with reference to the preferred embodiments. Obviously, modifications and alterations will occur to others upon a reading and understanding of the specification. It is intended to include all such modifications and alterations insofar as they come within the scope of the appended claims or the equivalents thereof.

Having thus described the invention, it is now claimed:

1. A blood pump comprising:
   a housing having an inlet and outlet communicating with a pump chamber defined therein;
   a rotor received in said pump chamber;
   rotating means located in a motor housing portion of the housing disposed adjacent the pump chamber for selectively rotating said rotor relative to the housing;
   a drive shaft interposed between said rotating means and said rotor for transferring drive motion from the rotating means to the rotor;
   a fluid seal means defined along said drive shaft for limiting blood flow from said pump chamber along said drive shaft and into the motor housing portion, said fluid seal means including a source of viscous biocompatible fluid adapted to flow through an opening receiving said drive shaft, the opening being dimensioned to define a nominal radial clearance on the order of one thousandth of an inch with said drive shaft; and means for pressurizing the biocompatible fluid to produce a leakage rate on the order of tenths of a cc/hr.

2. The blood pump as defined in claim 1 wherein said biocompatible fluid has a viscosity of approximately 5 or more centipoise.

3. The blood pump as defined in claim 1 wherein said clearance extends axially along said drive for a dimension approximating 0.05 to 1.00 inch.

4. The blood pump as define in claim 1 wherein said biocompatible fluid is glycerine.

5. The blood pump as defined in claim 1 wherein said biocompatible fluid is a glycerine or sugar solution with water or alcohol based solvents.

6. The blood pump as defined in claim 1 further comprising a secondary, contact-type seal member disposed between said rotating means and said fluid seal means for sealing the rotating means from the fluid seal means.

7. The blood pump as defined in claim 1 wherein said biocompatible fluid is a blood substitute emulsion.

8. The blood pump as defined in claim 1 further comprising a secondary seal interposed between said fluid seal means and said rotating means.

9. The blood pump as defined in claim 8 further comprising a fluid seal means inlet interposed between said secondary seal and said rotor.

10. The blood pump means as defined in claim 8 wherein said secondary seal is a contact-type seal member operatively engaging said drive shaft.

11. The blood pump as defined in claim 1 wherein said fluid seal means includes a labyrinth arrangement to control the flow of biocompatible fluid.

12. A blood pump comprising:
a housing having an inlet and outlet communicating with a pump chamber defined therein;
a rotor received in said pump chamber for conveying blood from said inlet to said outlet;
rotating means for rotating said rotor relative to the housing at a rotational speed on the order of 2000 to 12,000 rpm;
a drive member operatively extending between said rotating means and said rotor;
a fluid seal means adapted to seal along said drive member and inhibit blood flow from said pump chamber toward said rotating means, said fluid seal means including a source of biocompatible fluid having a viscosity of approximately 5 centipoise or greater and an opening receiving the drive member therethrough to define a clearance on the order of one thousandth of an inch with the drive member; and
contact seal means for sealing the rotating means from the fluid seal means and preventing inadvertent leakage of the biocompatible fluid from the housing.

13. The blood pump as defined in claim 12 wherein said biocompatible fluid is pressurized to produce a leakage rate into said pump chamber on the order of tenths of a cc/hour.

14. The blood pump as defined in claim 12 wherein the opening is defined by a series of variable diameter portions providing a non-uniform clearance along the drive member.

15. The blood pump as defined in claim 14 wherein the variable diameter portions generally increase in dimensions as the opening extends axially from the pump chamber.

16. The blood pump as defined in claim 12 wherein a portion of the opening includes a labyrinth arrangement for enhancing the sealing properties of the viscous fluid.

17. A blood pump comprising:
a housing having an inlet and outlet communicating with a pump chamber;
a rotor received in the pump chamber for pressurizing the blood between the inlet and the outlet;
a drive motor for rotating the rotor;
a drive shaft passing through a wall of the pump chamber and interconnecting the rotor to the drive motor;
fluid seal means for sealing along the drive shaft and preventing blood from the pump chamber from reaching the drive motor, the fluid seal means including (i) a source of biocompatible fluid having a viscosity of approximately 5 centipoise or greater, (ii) an opening in the wall of the pump chamber dimensioned to define a clearance on the order of one thousandth of an inch with the drive shaft and (iii) means for pressurizing the biocompatible fluid to produce flow through the clearance and into the pump chamber at a rate approximating 0.1 cc/hour; and
a contact seal engaging the drive shaft at a region on an opposite side of the fluid seal means from the pump chamber.

* * * * *